United States Patent [19]

Ravid et al.

[11] Patent Number: 4,986,278
[45] Date of Patent: Jan. 22, 1991

[54] BIOPSY SYRINGE DEVICE

[76] Inventors: Mordechai Ravid, Rekanti 3, Tel Aviv; Dan Kedem, Weizman 43, Rehovot 76283; Uzi Kedem, Gan Haim 44910, Israel

[21] Appl. No.: 452,078

[22] Filed: Dec. 18, 1989

[30] Foreign Application Priority Data

Jan. 13, 1989 [IL] Israel ........................................ 88947

[51] Int. Cl.$^5$ ............................................. A61B 10/00
[52] U.S. Cl. ................................... 128/753; 604/119; 604/121; 604/187; 604/220; 604/238; 604/256
[58] Field of Search .................. 128/749, 751–754, 128/760, 763, 765, 766; 604/118, 119, 121, 181, 187, 218, 220, 226, 236, 238, 240, 241, 256

[56] References Cited

U.S. PATENT DOCUMENTS 4,469,482  9/1984  Lissenburg et al. ................. 128/765

FOREIGN PATENT DOCUMENTS 0173653  3/1986  European Pat. Off. ............ 128/753

Primary Examiner—Randall L. Green
Assistant Examiner—Randy Shay
Attorney, Agent, or Firm—Benjamin J. Barish

[57] ABSTRACT

A biopsy syringe for removing a specimen from a subject includes a tubular housing having a long hollow needle and two pistons. The first piston carries a mandrel received in the hollow needle. The second piston defines a chamber between it and the first piston enabling the syringe to be pre-loaded with a vacuum which is manually controllable so as to permit the first piston to be actuated to a retracted position in a smooth and simple manner while holding the biopsy syringe.

17 Claims, 4 Drawing Sheets

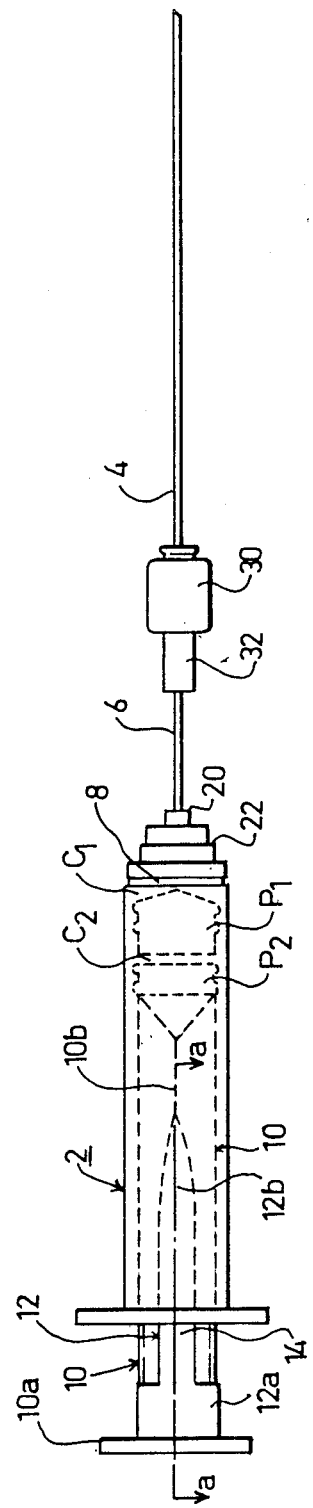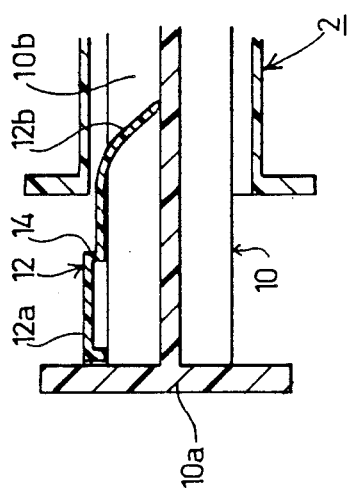

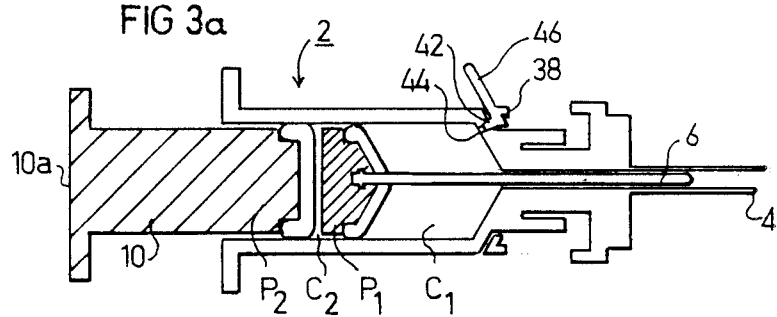
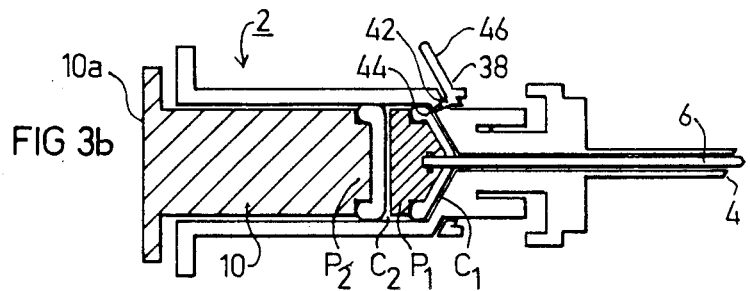
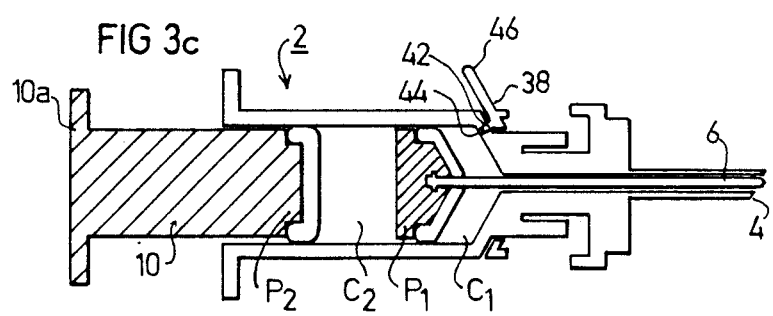
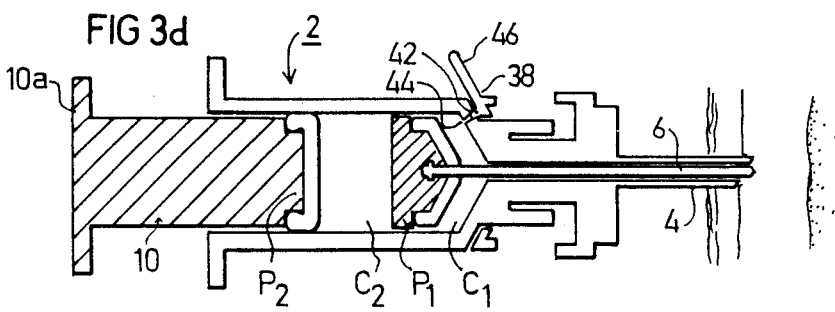

BIOPSY SYRINGE DEVICE

BACKGROUND OF THE INVENTION

The present invention relates to a biopsy syringe device for removing a biopsy specimen from a subject, and also to a method of using such a device.

A biopsy is a surgical procedure for removing a small sample of tissue from a person for the purpose of examining it under a microscope to see whether a disease is present. One common technique for performing a biopsy, particularly where the specimen to be removed is from the liver or kidney, is to use a biopsy syringe having a long hollow needle which is passed through the abdominal wall.

In using the conventional biopsy syringe for this purpose, the syringe is filled with about 3 cc saline before the hollow needle is passed through the abdominal wall. When the hollow needle has passed through the abdominal muscles and has entered the abdominal cavity surrounding the organ from which the specimen is to be removed (this being felt by the physician by the drop in force required to force the needle through the abdominal wall), about 2 cc of the saline are ejected through the hollow needle, and into the abdominal cavity in order to clean the needle of the tissue accumulated therein during its passage through the abdominal wall; the piston is then pulled back to a retracted position to create a vacuum therein; and the needle is then further pushed into the organ (e.g., liver, kidney, etc.) from which the specimen is to be taken, which specimen fills the interior of the hollow needle. The hollow needle is then withdrawn from the subject, and the remaining 1 cc saline water is used to expel the sample.

One serious drawback in the use of the conventional biopsy syringe for removing specimens in this manner is the difficulty for the physician to determine exactly when the needle has passed through the abdominal wall and into the abdominal cavity but has not yet entered the organ from which the biopsy specimen is to be removed. Thus, if the saline is ejected too soon, it will be injected into the muscle, such that subsequent uptake of the tissue sample will be of muscle tissue and not of the organ of choice; and if ejected too late, the saline may be injected into the organ itself which could cause damage. Another serious drawback is the difficulty for the physician to hold the device steady, particularly when moving the plunger rod in one direction to eject the 2 cc of saline after penetrating the abdominal muscles, and then moving the plunger rod in the reverse direction to create the vacuum, both movements being effected before entering the organ from which the specimen is to be taken. Thus, any slight lateral movement of the device at this critical time can cause considerable lateral movement of the needle tip within the organ which could result in considerable damage to the organ, accompanied by extensive internal bleeding due to the fact that the internal organs such as the liver, kidneys, etc., are soft tissues with a very extensive blood supply.

OBJECTS AND SUMMARY OF THE INVENTION

An object of the present invention is to provide a device particularly useful as a biopsy syringe needle for removing a specimen from a subject having advantages in the above respects. Another object of the invention is to provide a method of using such a biopsy syringe device for removing a specimen from a subject.

According to the present invention, there is provided a device particularly useful as a biopsy syringe for removing a specimen from a subject, comprising: a tubular housing; a long hollow needle extending from one end of the housing; and a first piston within the housing and defining a first chamber with the one end of the housing. The first piston carries a mandrel received in the hollow needle and has an outer diameter substantially equal to the inner diameter of the hollow needle. The first piston is movable within the housing to either an extended contracting the first chamber and locating the tip of the mandrel at or outwardly of the tip of the hollow needle, or to a retracted position expanding the first chamber and spacing the tip of the mandrel inwardly from the tip of said hollow needle. The device further includes a second piston within the housing between the opposite end thereof and the first piston and defining a second chamber therewith. The second piston is movable either to an extended position adjacent the first piston when in its extended position and thereby contracting the second chamber, or to a retracted position spaced away from the first piston When in its extended position and thereby expanding the second chamber to create a vacuum therein. Controllable venting means are provided for venting the first chamber to the atmosphere.

The invention also provides a method for removing a biopsy specimen from a subject by the use of the above-described device, comprising the steps: while the device is outside the subject's body, moving both the first and second pistons to their extended positions to contract both the first and second chambers and to cause the mandrel to occupy substantially the complete interior of the hollow needle; moving the second piston to its retracted position and retaining it in such position to expand the second chamber and thereby to create a vacuum therein, while the mandrel still occupies substantially the complete interior of the hollow needle; manually forcing the hollow needle and the mandrel therein through the abdominal wall of the subject until a lower resistance to such forcing is sensed, indicating that the tip of the needle has penetrated through the abdominal muscles and has entered the abdominal cavity surrounding the selected organ from which the biopsy specimen is to be removed; manually opening the venting means to vent the first chamber to the atmosphere, thereby causing the atmospheric pressure to move the first piston and mandrel to their retracted positions, creating a vacuum at the top of the hollow needle; continuing to force the hollow needle into the selected organ to cause a specimen thereof to be received within the hollow needle; withdrawing the hollow needle from the subject with the specimen therein; and moving the second piston against the first piston to cause both to be moved to their extended positions to expel the specimen from the hollow needle.

It will thus be seen that the use of the device of the present invention for removing a biopsy specimen does not require the ejection of saline solution when the needle is in the subject's body. Using the novel biopsy syringe therefore avoids the possibility of injecting the saline solution either too early which would result in partially or completely filling the hollow needle with muscle tissue rather than the organ tissue to be sampled, or too late which might result in damage to the organ to be sampled. The use of the novel device also avoids the awkward bidirectional movements presently required by the physician when using the conventional biopsy syringe, and thereby minimizes the possibility of causing the needle tip, when in the organ of choice, to move laterally and to internally injure the subject.

Further features and advantages of the invention will be apparent from the description below.

BRIEF DESCRIPTION OF THE DRAWINGS

The invention is herein described, by way of example only, with reference to the accompanying drawings, wherein:

FIG. 1 illustrates One form of biopsy syringe device constructed in accordance with the present invention;

FIG. 1a is a sectional view along line a—a of FIG. 1;

FIGS. 3a–3h illustrate the procedure for using the device of FIG. 1 in order to remove a biopsy specimen from a subject.

DESCRIPTION OF A PREFERRED EMBODIMENT

Figure 2:
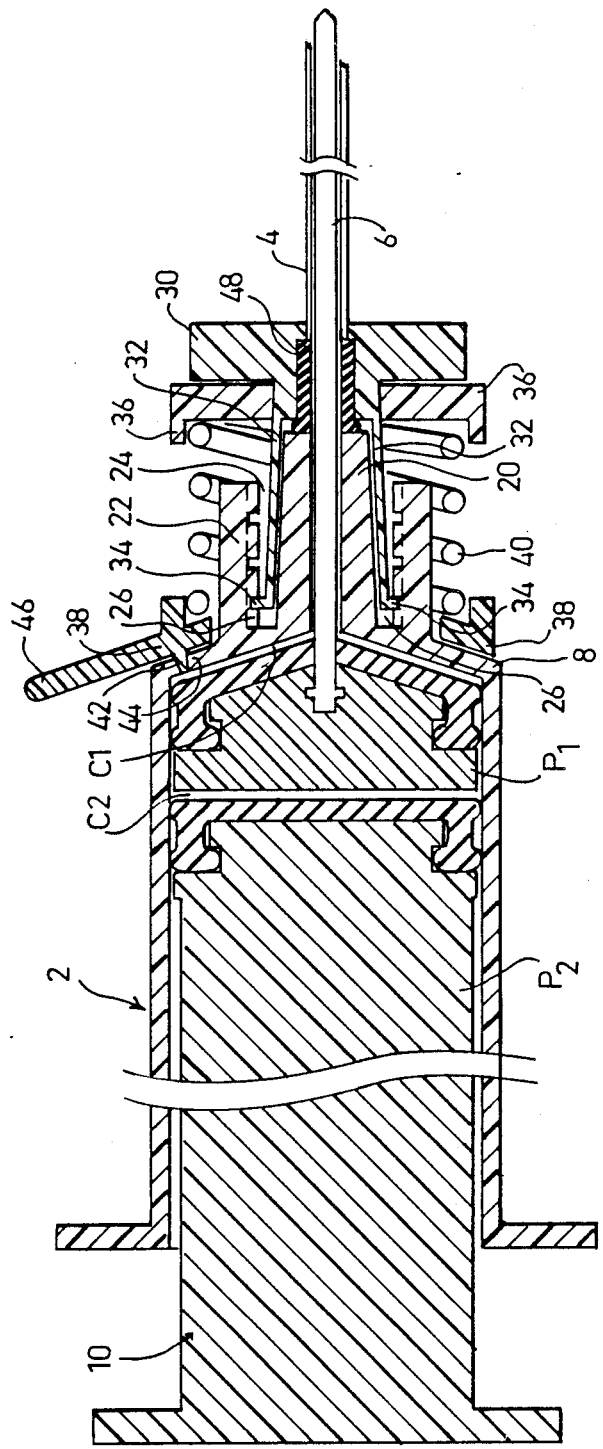
FIG. 2 is an enlarged sectional view of the device of FIG. 1.

The device illustrated in FIGS. 1 and 2 of the drawings is particularly useful as a biopsy syringe for removing a specimen from an organ, such as the liver or kidney, of a subject in order to permit examination of the specimen.

The illustrated device comprises a tubular housing 2 of the type used in a conventional syringe, except that there are two pistons $P_1$, $P_2$ movable within the housing. The device further includes a long hollow needle 4 extending from one end of the housing, and a mandrel 6 having one end fixed to piston $P_1$ and the opposite end extending through the hollow needle 4. The outer diameter of mandrel 6 is substantially equal to the inner diameter of the hollow needle 4 so that the mandrel substantially fills the interior of the hollow needle but is freely movable therein.

Figure 3E:
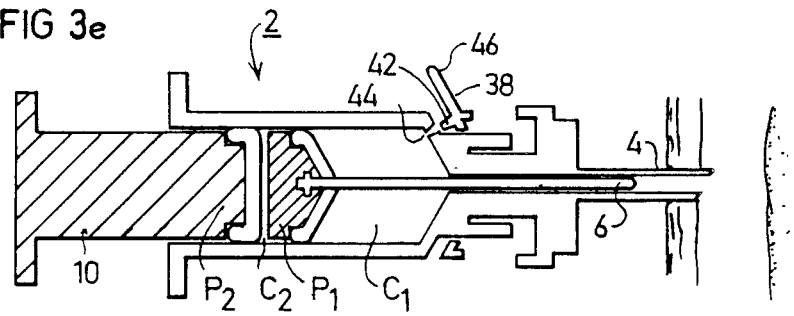

Piston $P_1$ defines a first chamber $C_1$ between it and end wall 8 of the housing through which mandrel 6 passes. Another chamber $C_2$ is defined between piston $P_1$ and the second piston $P_2$. Both pistons $P_1$ and $P_2$ are movable individually to a retracted position, as shown for example in FIG. 3a, or to an extended position, as shown in FIGS. 2 or 3b, wherein both chambers $C_1$ and $C_2$ are in a contracted condition.

Piston $P_2$ includes a plunger rod 10 projecting through the end of housing 2 opposite to end wall 8, and manually grippable by the user in order to move piston $P_2$ to its retracted position, i.e., in the direction away from end wall 8. Piston $P_2$ may be retained in its retracted position by a manually-releasable retainer member 12 in the form of a flexible plastic clip carried by plunger rod 10 and formed with a shoulder 14, engageable with the outer end of housing 2 when the plunger rod is extended, as shown in FIGS. 1 and 1a. One end 12a of clip 12 encloses the plunger rod and abuts against head 10a of the rod, whereas the opposite end 12b is pointed and is received in a recess 10b formed in the plunger rod.

The arrangement is such that pulling out the plunger rod 10 causes its shoulder 14 to abut against the outer edge of housing 2 to retain the plunger rod and its piston $P_2$ in its retracted position, but merely pressing clip 12 at the point outwardly of its shoulder 14, releases the plunger rod and its piston $P_2$.

When piston $P_2$ is in the above-described retracted position, and piston $P_1$ is in its extended position (that illustrated in FIGS. 2 or 3c), chamber $C_2$ is expanded, thereby creating a vacuum in that chamber. As will be described below, such a vacuum is produced before the hollow needle 4 of the device is caused to penetrate the subject's abdominal muscles, and the vacuum so produced is exploited to move piston $P_1$ to its retracted position after such penetration has occurred in order to cause a specimen of the selected organ to fill the tip of the needle.

End wall 8 of the tubular housing 2 is integrally formed with an axially-extending stem 20 having a central opening receiving the mandrel 6. The outer face of stem 20 is of conical configuration, decreasing in diameter from end wall 8. End wall 8 is further integrally formed with an annulus 22 circumscribing stem 20 but of slightly shorter length than the stem and spaced from it by an annular space 24. The inner face of annulus 22 is formed with a pair of axially-extending bayonet slots 26.

The hollow needle 4 is carried by a collar 30 removably attached to end wall 8 of the tubular housing 2 by a conical extension 32 received within the annular space 24 between stem 20 and annulus 22. The inner end of the collar extension 32 is formed with a pair of outwardly-bent tabs 34 serving as pins cooperable with bayonet slots 26 in annulus 22 for releasably securing collar 30 to the end wall 8.

A ring 36 is received over extension 32 of collar 30, and a cap 38 is applied over the end wall 8 of the tubular housing 2. Cap 38 is pressed against the end wall by a coiled spring 40 interposed between the cap and ring 36. Cap 38 is formed with an inwardly-directed plug 42 which serves a closure member for closing a venting port 44 formed in end wall 8. Plug 42 is normally urged to its closed position within the venting port 44 by the coiled spring 40, but may be manually moved out of the venting port by manually pressing against a lever 46 integrally formed with cap 38.

As will be described more particularly below, port 44 acts as a venting port for venting to the atmosphere chamber $C_1$ between piston $P_1$ and the housing end wall 8. When manual lever 46 is pressed (rightwardly in FIG. 2), plug 42 is withdrawn from port 44, thereby subjecting chamber $C_1$ to atmosphere pressure.

Collar 30 further includes a sealing ring 48 formed with a central opening through which mandrel 6 passes. The inner end of sealing ring 48 engages, and is pressed against the outer surface of stem 20 when collar 30 carrying the hollow needle 4 is attached to the end wall, as shown in FIG. 2, thereby enhancing the seal of the respective end of hollow needle 4 from the atmosphere and from chamber $C_1$.

The illustrated biopsy syringe may be used for removing a specimen from a subject's organ, such as the liver or kidney, in the following manner:

The two pistons $P_1$ and $P_2$, first in their retracted positions as illustrated in FIG. 3a, are moved to their extended positions (FIG. 3b) wherein mandrel 6 occupies the interior of the hollow needle 4. In this position, both of the chambers $C_1$ and $C_2$ are contracted, and the mandrel 6 is moved so that its outer tip is located substantially at or projecting slightly outwardly of the outer tip of the hollow needle 4, i.e., the mandrel occupies substantially the complete interior of the hollow needle.

Piston $P_2$ is then moved to its retracted position (FIG. 3c) and is retained in such position by retainer clip 12 (FIGS. 1 and 1a). This movement of piston $P_2$ expands chamber $C_2$ and creates a vacuum therein, the vacuum created in chamber $C_2$ moving piston $P_1$ only slightly from its extended position because of a corresponding vacuum created in chamber $C_1$ by the latter movement of piston $P_1$ from its extended position, as shown in FIG. 3c. Thus, mandrel 6 still occupies substantially the complete interior of needle 4.

This is the "pre-loaded" condition of the biopsy syringe; that is, it is "pre-loaded" with a vacuum in chamber $C_2$ (and also with a vacuum in chamber $C_1$.

The physician then makes a small incision at the site of the selected organ (e.g., liver, kidney) from which the biopsy specimen is to be removed, and forces the hollow needle 4 through the incision. Since the mandrel 6 still occupies substantially the complete interior of the hollow needle, no muscle tissue enters the hollow needle during this penetration. The physician forces the needle through the abdominal wall until the resistance to such forcing drops, indicating that the tip of the needle has penetrated through the abdominal muscles and has entered the abdominal cavity surrounding the tissue from which the biopsy specimen is to be removed (FIG. 3d).

At that time, the physician presses forwardly (rightwardly, FIG. 3d) lever 46 to remove plug 42 from vent port 44, thereby venting chamber $C_1$ to the atmosphere. Since piston $P_1$ is now no longer subject to a vacuum in chamber $C_1$, the vacuum in chamber $C_2$ draws piston $P_1$ to its retracted position, and retracts the mandrel 6 within needle 4 (FIG. 3e), thereby creating a vacuum between the retracted tip of the mandrel 6 and the tip of the needle 4.

Figure 3F:
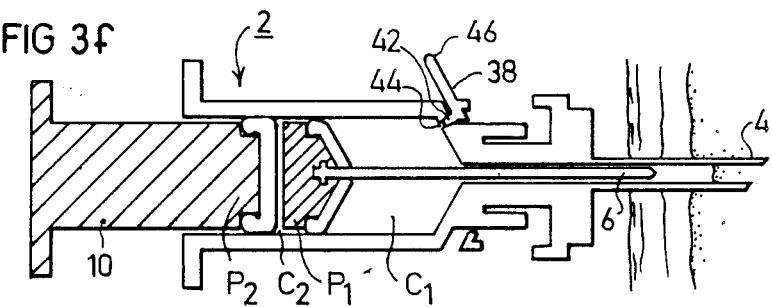
Figure 3G:
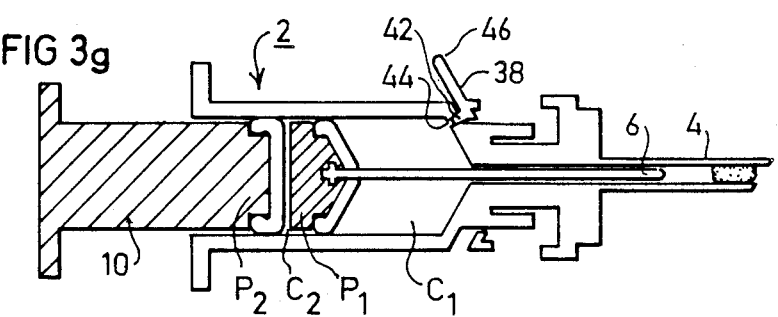
Figure 3H:
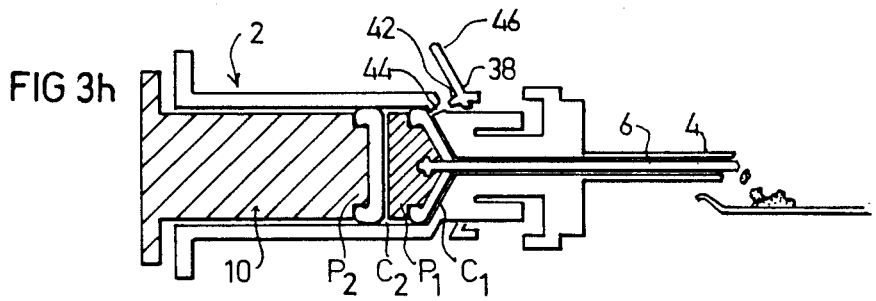

The physician then continues to force the hollow needle 4 through the tissue to cause a specimen of the tissue to be received within the needle (FIG. 3f). The needle is then withdrawn from the subject with the tissue specimen therein (FIG. 3g). When the needle has thus been withdrawn, the physician manually moves piston $P_2$ against piston $P_1$, bringing both to their extended positions thereby causing the mandrel 6 to expel the tissue specimen from the interior of the hollow needle 4 (FIG. 3h).

It will thus be seen that the use of the biopsy syringe illustrated in the drawings does not require the injection of saline solution in order to clean the interior of the hollow needle after it has penetrated through the abdominal muscles and is about to enter the organ from which the biopsy specimen is to be taken. This is because the mandrel 6 is located within the hollow needle 4 at this time, and therefore prevents the muscle or other tissue from entering the hollow needle. Accordingly, the danger, characteristic of the previously used biopsy syringes, of not ejecting saline solution to clean the hollow needle at the proper time (i.e., after the tip of the hollow needle has cleared the abdominal muscles but has not yet entered the organ from which the specimen is to be taken) is not present when using the biopsy syringe illustrated in the drawings.

It will also be seen that the awkwardness of manipulating the biopsy syringe, characteristic of the previously known biopsy syringes wherein the saline solution had to be ejected at a critical time when the needle was inserted into the patient's body, is also avoided by the biopsy syringe illustrated in the drawings. This is because the illustrated biopsy syringe permits "pre-loading" it with the vacuum in chamber $C_2$ before the needle is inserted into the subject's body, and permits the piston $P_1$ to be actuated to its retracted position merely by pressing forward lever arm 46, which can be done in a smooth and simple manner without changing hands or making any other awkward movements while holding the biopsy syringe. Accordingly, the use of the illustrated biopsy syringe substantially reduces the danger of inadvertently moving the hollow needle 4 laterally after it has been inserted into the organ, which might cause it to extensively injure the delicate tissue of the organ.

While the invention has been described with respect to one preferred embodiment, it will be appreciated that many variations, modifications and other applications of the invention may be made.

What is claimed is:

1. A device particularly useful as a biopsy syringe for removing a specimen from a subject, comprising:
    a tubular housing;
    a long hollow needle extending from one end of said housing;
    a first piston within said housing and defining a first chamber with said one end of the housing; said first piston carrying a mandrel received in the hollow needle and having an outer diameter substantially equal to the inner diameter of the hollow needle; said first piston being movable within said housing to either an extended position contracting said first chamber and locating the tip of said mandrel at or outwardly of the tip of said hollow needle, or to a retracted position expanding said first chamber and spacing the tip of said mandrel inwardly from the tip of said hollow needle;
    a second piston within said housing between the opposite end thereof and said first piston and defining a second chamber therewith; said second piston being movable either to an extended position adjacent said first piston when in its extended position and thereby contracting said second chamber, or to a retracted position spaced away from said first piston when in its extended position and thereby expanding said second chamber to create a vacuum therein;
    and controllable venting means for venting said first chamber to the atmosphere.

2. The device according to claim 1, further including manually-releasable retaining means for retaining said second piston in its retracted position when said first piston is in its extended position producing a vacuum in said second chamber.

3. The device according to claim 2, wherein said manually-releasable retaining means comprises a plunger rod secured to said second piston and extending through the end of said housing opposite to said first end thereof; and a manually-releasable retainer clip engageable with said plunger rod for retaining it and said second piston in the retracted position of said second piston.

4. The device according to claim 1; wherein said housing includes an end wall at said one end thereof defining one end of said first chamber, and said venting means comprises a venting port in said end wall, a closure member normally closing said venting port, and a fingerpiece for moving said closure member to open said venting port.

5. The device according to claim 4, wherein said hollow needle is secured to a collar attachable to said end wall of the housing; said device further including a spring between said collar and said closure member normally urging said closure member to its closed position with respect to said venting port.

6. The device according to claim 5, wherein said end wall includes an axially-extending stem formed with a central opening through which said mandrel passes, said stem being circumscribed by an axially-extending annulus radially spaced from said stem for removably receiving said collar and the hollow needle secured thereto.

7. The device according to claim 6, wherein said collar is integrally formed with an extension for releasably attaching the collar, and the needle carried thereby, in the space between said stem and annulus.

8. The device according to claim 7, wherein said annulus is formed with internal threads, and said collar extension is formed with an outturned tip received in said internal threads.

9. The device according to claim 8, wherein said collar includes a sealing ring formed with an opening for receiving said mandrel and engageable with said stem to effect a seal between the interior of said first chamber and the interior of said hollow needle.

10. A device particularly useful as a biopsy syringe for removing a specimen from a subject, comprising:
   a tubular housing;
   a long hollow needle extending from one end of said housing;
   a first piston within said housing and defining a first chamber with said one end of the housing; said first piston carrying a mandrel received in the hollow needle and having an outer diameter substantially equal to the inner diameter of the hollow needle; said first piston being movable within said housing to either an extended position contracting said first chamber and locating the tip of said mandrel at or outwardly of the tip of said hollow needle, or to a retracted position expanding said first chamber and spacing the tip of said mandrel inwardly from the tip of said hollow needle;
   a second piston within said housing between the opposite end thereof and said first piston and defining a second chamber therewith; said second piston being movable either to an extended position adjacent said first piston when in its extended position and thereby contracting said second chamber, or to a retracted position spaced away from said first piston when in its extended position and thereby expanding said second chamber to create a vacuum therein;
   and controllable venting means for venting said first chamber to the atmosphere;
   said housing including an end wall at said one end thereof defining one end of said first chamber, and said venting means comprising a venting port in said end wall, a closure member normally closing said venting port, and a fingerpiece for moving said closure member to open said venting port.

11. The device according to claim 10, further including manually-releasable retaining means for retaining said second piston in its retracted position when said first piston is in its extended position producing a vacuum in said second chamber.

12. The device according to claim 11, wherein said manually-releasable retaining means comprises a plunger rod secured to said second piston and extending through the end of said housing opposite to said first end thereof; and a manually-releasable retainer clip engageable with said plunger rod for retaining it and said second piston in the retracted position of said second piston.

13. The device according to claim 12, wherein said hollow needle is secured to a collar attachable to said end wall of the housing; said device further including a spring between said collar and said closure member normally urging said closure member to its closed position with respect to said venting port.

14. The device according to claim 13, wherein said end wall includes an axially-extending stem formed with a central opening through which said mandrel passes, said stem being circumscribed by an axially-extending annulus radially spaced from said stem for removably receiving said collar and the hollow needle secured thereto.

15. The device according to claim 14, wherein said collar is integrally formed with an extension for releasably attaching the collar, and the needle carried thereby, in the space between said stem and annulus.

16. The device according to claim 15, wherein said annulus is formed with internal threads, and said collar extension is formed with an outturned tip received in said internal threads.

17. The device according to claim 16, wherein said collar includes a sealing ring formed with an opening for receiving said mandrel and engageable with said stem to effect a seal between the interior of said first chamber and the interior of said hollow needle.

* * * * *